United States Patent [19]

Anteunis et al.

[11] Patent Number: 4,725,645

[45] Date of Patent: Feb. 16, 1988

[54] PROCESS FOR SYNTHESISING PEPTIDES

[75] Inventors: Marc Anteunis; Christian Becu, both of Gand, Belgium

[73] Assignee: Solvay & Cie. (Société Anonyme), Brussels, Belgium

[21] Appl. No.: 800,901

[22] Filed: Nov. 22, 1985

[30] Foreign Application Priority Data

Nov. 23, 1984 [FR] France ............................ 84 18011

[51] Int. Cl.$^4$ .................... A61K 37/02; C08F 283/00
[52] U.S. Cl. ............................ 525/54.11; 525/54.1; 530/334
[58] Field of Search ........................ 525/54.1, 54.11; 530/333, 334

[56] References Cited

U.S. PATENT DOCUMENTS 3,988,304 10/1976 Gersky .................. 525/54.1
4,127,539 11/1978 Coy et al. ............ 525/54.11

FOREIGN PATENT DOCUMENTS 0084941 1/1983 European Pat. Off. ........... 02001977/FRX
0099709 7/1983 European Pat. Off. .

OTHER PUBLICATIONS

Chemical Abstracts, vol. 100, no. 12, Mar. 19th, 1984, p. 14, no. 86324b, Columbus, Ohio, US.
Y. Nakayama et al., "Novel Synthesis of alpha-amino acids via Cyanosilylation of Schiff Bases". Agr. Biol. Chem., vol. 39, no. 2, Feb. 1975, pp. 571-572. Edit. Agric. Chem. Soc. Tokyo, Japan.
R. L. Johnson, "Renin Inhibitors. Substitution of the Leucyl Residues of Leu-Leu-Val-Phe-OCH3 with 3-amino-2-hydroxyl-5-methylhexanoic acid" Journal of Medicinal Chemistry, vol. 25, No. 5, May 1982, pp. 605-610. American Chemical Society, US.
H. R. Kricheldorf, Liebigs Ann. Chem. 763, pp. 17-38 (1972).
Leonhard Birkofer et al., Chem. Ber, 94, pp. 1263-1267 (1961).
Leonhard Birkofer et al., Liebigs Ann. Chem., 659, pp. 190-199, (1962).
S. V. Rogozhin et al., Seriya Khimicheskaya, N. 3, pp. 657-660, (Mar. 1977).

Primary Examiner—Delbert R. Phillips
Assistant Examiner—Nathan M. Nutter
Attorney, Agent, or Firm—Spencer & Frank

[57] ABSTRACT

The process enables peptides to be synthesized from amino acids with the participation of trialkylcyanosilanes.

The peptides obtained by this synthesis route are used, in particular, in pharmaceutical applications.

7 Claims, No Drawings

PROCESS FOR SYNTHESISING PEPTIDES

The present invention relates to a process for synthesising peptides from amino acids, with the participation of trialkylcyanosilanes.

The silylation of amino acids to prepare peptides by reaction of a amino acid, the —NH$_2$ function of which is blocked and the —COOH function of which is activated, with another amino acid which has been silylated with the participation of silylating agents such as trimethylchlorosilane, has been described by Kricheldorf H. R., Liebigs Ann., 1972, 763, p. 17–38.

Furthermore, other silylating agents such as hexamethylsilazane (Birkofer L., Konkol W. and Ritter A., Chem. Ber. 1961, 94, p. 1263–1267 and Birkofer L., Ritter A. and Neuhausen P., Liebigs Ann. Chem., 1962, 659, p. 190–199) and N-(trimethylsilyl)diethylamine and N,O-bis(trimethylsilyl)acetamide (S. V. Rogozhin, Yu. A. Davidovich, A. I. Yurtanov, Seriya Khimicheskaya, N. 3, p. 657–660, March 1977—Original article Oct. 27, 1976) have also been made known for this same reaction.

The various silylating agents used hitherto nevertheless possess various disadvantages. In effect, these agents generally require the presence of a base which must be removed subsequently, and which frequently causes racemisation of the amino acids during the coupling stage or internal cyclisation at the dipeptide stage. Moreover, by-products are formed during the silylation and the reaction is generally incomplete, and this leads to poor yields, frequently of less that 50%.

Another disadvantage of the silylating agents of the prior art results from the presence of water, which decomposes the alkylsilyl reagents with the formation of the corresponding hexaalkyldisiloxane.

Furthermore, the silylated derivatives are formed in a separate stage, and have to be isolated before the coupling stage.

In the processes of the prior art, peptide synthesis is, moreover, greatly limited by the problems of solubility of the peptides formed when their molecular weight increases. The synthesis is hence frequently limited by the low solubilities of the intermediate products during the coupling reactions, and by the difficulties in purifying the final products. The longer the peptide chain, the more complex the problems become.

Furthermore, some particular silylating agents of the prior art present specific problems. Thus, the use of hexamethyldisilazane, a more nucleophilic reagent than the desired silylated amino compound, causes side reactions which affect the yield of the process. The use of trimethylchlorosilane is incompatible with the protection of the —NH$_2$ groups of the amino acids with benzyloxycarbonyl type groups.

The process of the present invention relates to carrying out peptide synthesis from amino acids by means of silylating agents which do not have the disadvantages of the known processes.

More especially, the process makes it possible to carry out a rapid coupling reaction in continuous fashion, which reaction takes place without racemisation and can be carried out in the absence of basic coreagents, with water optionally present and in the presence of known protecting agents. In addition, it enables peptides of high molecular weight to be produced in yields higher than those obtained with the known silylating agents. Moreover, the process of the invention enables the water to be chemically consumed and volatile silyl derivatives to be obtained, which facilitates removal of the latter.

To this end, the present invention relates to a process for synthesising peptides from amino acids,—optionally—combined and/or substituted, using trialkylsilane derivatives, wherein there are used, as trialkylsilanes, trialkylcyanosilanes of general formula (A)

in which R$_1$, R$_2$ and R$_3$ denote, independently of each other, alkyl groups which can be identical or different and which contain from 1 to 3 carbon atoms. Usually, the groups R$_1$, R$_2$ and R$_3$ denote alkyl groups containing 1 or 2 carbon atoms. Finally, R$_1$, R$_2$ and R$_3$ preferably denote identical alkyl groups. Trimethylcyanosilane is most especially preferred.

The trialkylcyanosilanes used in the process according to the invention are preferably volatile products which can be readily removed. These silylating agents possess solubilisation properties superior to those of the usual silylating agents, and this enables them to be used simultaneously as a reagent for forming the peptide link between the amino acids and as a solvent for the amino acids and peptides.

The trialkylcyanosilanes can be employed alone or in the presence of a solvent intermediary. And the latter can, for example, originate from the activation stage or they can be added conjointly during the coupling stage. However, it is preferable to carry out the coupling stage without adding a solvent intermediary.

Solvent intermediaries which have given good results when used in conjunction with trimethylcyanosilane are, in particular, dichloromethane and tetrahydrofuran.

The amount of trialkylcyanosilanes used in the process according to the invention can vary within wide limits. In general, from 20 to 0.01 ml of trialkylcyanosilane are employed per mmol of amino acid. In the case of trimethylcyanosilane, from 5 to 0.1 ml of trimethylcyanosilane are preferably employed per mmol of amino acid employed.

As amino acids, it is possible to use any combined and/or substituted amino acid possessing at least one carboxyl function and at least one primary or secondary amino function, such as known natural amino acids or synthetic amino acids which are not naturally-occurring. As natural amino acids there are used generally linear, branched or cyclic aliphatic amino acids such as amino acids possessing a hydrocarbon chain, hydroxylated or sulphur-containing amino acids, dicarboxylic amino acids, basic amino acids and aromatic or heterocyclic amino acids.

By combined amino acid, there is understood any compound resulting from the reaction of an amino acid, through at least one of its carboxyl functions and/or amine functions, as defined above with an entity with which this function is reactive. Among preferred combined amino acids, there are understood molecules such as small peptides containing a succession of 2, 3 or more amino acids which are identical or different in chemical nature.

By substituted amino acid, there is understood any compound of the amino acid or combined amino acid type, as defined above, containing organic or inorganic substituents in place of one or more hydrogen atoms linked to carbon atoms. These organic or inorganic substituents can be simple or complex, and substituted or unsubstituted, and comprise, in particular, chlorine and fluorine atoms, as well as aliphatic and aromatic groups such as alkyl, alkenyl, cycloalkyl, benzyl, phenyl, naphthyl and pyridyl groups, and the like.

The other operating conditions used in the process according to the invention are not critical; thus, the pressure at which the process is performed is generally between 0.1 and 10 bars. Good results have been obtained at atmospheric pressure. The temperature at which the process is performed is such that the silylating agent used remains liquid at the pressure in question. It is usually less than 100° C. At atmospheric pressure, when trimethylcyanosilane is employed as the silylating agent, the temperature of the coupling stage is less than 40° C., and good results have been obtained at room temperature.

The process can be carried out in any apparatus designed for this purpose.

The synthetic scheme for the process according to the present invention is given below.

In this scheme, $A_1$, $A'_1$ and $A_2$ denote amino acid residues of any kind, either natural or synthetic. It should be noted that the principle of the scheme, although established for amino acids having a primary amine function, also applies in the case of amino acids containing a secondary amine function, such as proline and hydroxyproline; in this case, it is sufficient to replace the function $-NH_2$ by a function $>NH$ in the scheme below.

SYNTHETIC ROUTE

1.—protection of the amine function of a first amino acid by a classical protecting agent such as, for example, protection by benzyloxycarbonyl (hereinafter designated Z) or tert-butyloxycarbonyl (t-Boc) type groups, according to the schemes:

amino acid ⟶ protected amino acid

$NH_2-A_1-COOH \xrightarrow{Z} Z-NH-A_1-COOH$

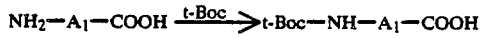

$NH_2-A_1-COOH \xrightarrow{t\text{-Boc}} t\text{-Boc}-NH-A_1-COOH$

2.—activation of the carboxyl function by a classical activating agent such as, for example, activation by conversion to the acid chloride or anhydride (Act) according to the schemes:

-protected amino acid ⟶ protected and activated amino acid

$Z-NH-A_1-COOH \longrightarrow Z-NH-A_1-COOAct$ (I)

$t\text{-Boc}-NH-A_1-COOH \longrightarrow t\text{-Boc}-NH-A_1-COOAct$ (I)'

It should be noted, however, that in certain cases it is possible to carry out the activation starting with protected amino acids in which the carboxyl function is substituted. An example of this type is the silylated N-protected amino acids obtained by prior silylation with trimethylcyanosilane (TMSCN), according to the scheme:

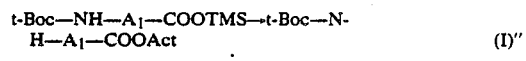

$t\text{-Boc}-NH-A_1-COOTMS \rightarrow t\text{-Boc}-NH-A_1-COOAct$ (I)''

3.—silylation of a second amino acid by reaction with a trialkylcyanosilane such as trimethylcyanosilane (TMSCN) according to the scheme:

amino acid ⟶ silylated amino acid

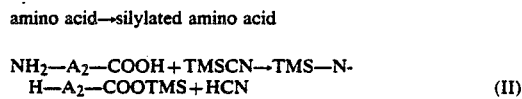

$NH_2-A_2-COOH + TMSCN \rightarrow TMS-NH-A_2-COOTMS + HCN$ (II)

It is, however, obvious that the distinction between stages 1, 2 and 3 is purely formal, since these stages can be carried out independently of each other. Thus, it is of no consequence whether stage 3, for example, follows or preceeds stages 1 and 2.

4.—coupling with formation of a peptide by reaction between the protected and activated amino acid (I) or (I)' and the silylated amino acid (II) according to the schemes

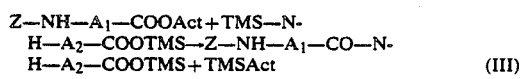

$Z-NH-A_1-COOAct + TMS-NH-A_2-COOTMS \rightarrow Z-NH-A_1-CO-NH-A_2-COOTMS + TMSAct$ (III)

or

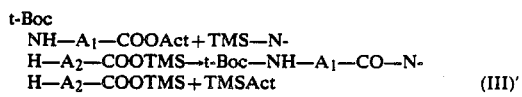

$t\text{-Boc}-NH-A_1-COOAct + TMS-NH-A_2-COOTMS \rightarrow t\text{-Boc}-NH-A_1-CO-NH-A_2-COOTMS + TMSAct$ (III)'

5.—desilylation of the peptide (III) or (III)' obtained by displacement of the trialkylsilane group and formation of the carboxylic acid ($-COOH$) group, for example by a treatment in a methanolic medium or in the presence of water. This reaction takes place according to the schemes:

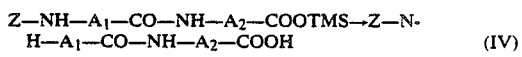

$Z-NH-A_1-CO-NH-A_2-COOTMS \rightarrow Z-NH-A_1-CO-NH-A_2-COOH$ (IV)

or

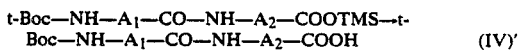

$t\text{-Boc}-NH-A_1-CO-NH-A_2-COOTMS \rightarrow t\text{-Boc}-NH-A_1-CO-NH-A_2-COOH$ (IV)'

Stages 5 and 6 can be carried out at the same time or successively.

6.—deprotection of the peptide (IV) or (IV)' obtained. This deprotection can be carried out by displacement of the protecting agent and formation of the amine group ($NH_2$) by any known method, such as, for example, by bubbling hydrogen chloride gas through a dichloromethane and/or tetrahydrofuran solution, or by trifluoroacetic acid in dichloromethane followed by passage of the peptides, in the form of salts, through a column for exchanging acidic ions. This operation can be illustrated by the following general schemes:

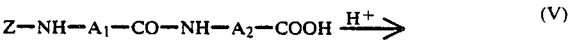

$Z-NH-A_1-CO-NH-A_2-COOH \xrightarrow{H^+}$ (V)

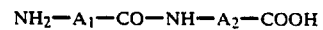

$NH_2-A_1-CO-NH-A_2-COOH$

-continued $$\text{t-Boc—NH—A}_1\text{—CO—NH—A}_2\text{—COOH} \longrightarrow \quad (V)'$$

$$\text{NH}_2\text{—A}_1\text{—CO—NH—A}_2\text{—COOH}$$

When it is desired to carry out successive couplings of amino acids, stages 5 and/or 6 are not always necessary. In this case, two routes are possible, that is to say neither starting from the carboxyl terminus and proceeding towards the amine terminus, or by starting from the amine terminus and proceeding towards the carboxyl terminus.

According to the first route, the product (V) is silylated according to the scheme:

$$\text{NH}_2\text{—A}_1\text{—CO—NH—A}_2\text{—COOH} + \text{TMSCN} \rightarrow \text{T-MS—NH—A}_1\text{—CO—NH—A}_2\text{—COOTMS} \quad (VI)$$

and this product (VI) is then combined with a protected and activated amino acid of the type (I) and (I)'.

According to the second route, the product (V) obtained is protected and activated according to the schemes described in stages 1 and 2 above, and the product obtained is reacted with a new amino acid which is trimethylsilylated on the amine and carboxyl functions, of formula (II).

An example of a scheme for this second case can be as follows:

$$\text{t-Boc—NH—A}_1\text{—CONH—A}_1'\text{—COOH} \xrightarrow{\text{Activation}}$$

$$\text{t-Boc—NH—A}_1\text{—CONH—A}_1'\text{—COOAct}$$

$$\text{t-Boc—NH—A}_1\text{—CONH—A}_1'\text{—COOAct} +$$

$$\text{TMSNH—A}_2\text{—COOTMS} \xrightarrow{\text{TMSCN in excess}}$$

$$\text{t-Boc—NH—A}_1\text{—CONH—A}_1'\text{—CONH—A}_2\text{—COOTMS}$$

As a result of using trialkylcyanosilanes of general formula (A), the processes shown schematically above make it possible to obtain peptides of natural type or synthetic peptides which do not have their equivalent in nature.

These known or new peptides obtained according to the process of the invention can be used in various applications such as, in particular, enzymic catalysis, as nutrient constituents, or as pharmaceutical products for veterinary or human use.

The examples which follow serve to illustrate the invention. In these examples, the following abbreviations have been used:

| | |
|---|---|
| Ala | alanine |
| Asp | aspartic acid |
| Cys | cysteine |
| Gly | glycine |
| Met | methionine |
| Phe | phenylalanine |
| Pro | proline |
| Ser | serine |
| Thr | threonine |
| Thz | gamma-thiaproline |
| Tyr | tyrosine |
| Val | valine |
| O Piv | pivaloyloxy(trimethylacetyloxy) |
| O Succ | N—hydroxysuccinimide |

EXAMPLE 1 coupling of a peptide with an activated amino acid and a silylated amino acid 1.a: glycine-cysteine To 1.1 mmol of lyophilised hydrated cysteine thee is added 0.5 ml of trimethylcyanosilane in a thick-walled test tube fitted with a stopper. The mixture is subjected to ultrasound (sonicator) until a clear solution is obtained. The mixture is heated to between 60° and 80° C. for 5 minutes until the amino acid has dissolved.

1 mmol of glycine, protected by Z (benzyloxycarbonyl group) and activated by 0 Succ in the presence of N,N'-dicyclohexylcarbodiimide, and obtained in a previous stage, is added.

The coupling between the silylated cysteine and the protected and activated glycine is accelerated by gentle heating to 40° C., and has finished after 1 hour at room temperature.

The reaction is stopped by adding 10 ml of water. The solution is then lyophilised and the lyophilisate is mixed with n-hexane.

After addition of 10 ml of water to re-suspend the product, the latter is centrifuged and the collected precipitate is dried.

The yield of formation of protected peptide is virtually quantitative (Z—Gly—CysOH) without contamination by epimers (nuclear magnetic resonance (NMR)<5%), and the protecting agent Z is finally released by bubbling hydrogen chloride gas into dichloromethane containing the protected peptide, with the formation of the dipeptide Gly-CysOH.HCL (hydrochloride of the dipeptide).

1.b: Glycine-Clycine

The formation of Z—Gly—GlyOH is obtained by the same process as that described in Example 1.a, but using 1.1 mmol of lyophilised hydrated glycine in place of cysteine.

1.c: Alanine-Serine

The formation of Z—Ala—SerOH is obtained by the same process as that described in Example 1.a, but using 1.1 mmol of lyophilised hydrated serine in place of cysteine and 1 mmol of alanine protected by Z and activated in place of glycine.

1.d: Phenylalanine-Serine

The formation of t-Boc—Phe—SerOH is obtained by the same process, but using 1.1 mmol of lyophilised hydrated serine in place of cysteine and 1 mmol of phenylalanine protected by t-Box and activated in place of glycine.

The group protected by t-Boc is released by treatment with trifluoroacetic acid followed by evaporation.

1.e: Proline-Phenylalanine

The formation of t-Boc—Pro—PheOH is obtained by the same process but using 1.1 mmol of lyophilised hydrated phenylalanine in place of cysteine and 1 mmol of proline protected by t-Boc and activated in place of glycine.

EXAMPLE 2

Repeated condensation without purification of he intermediate peptides

Preparation of Z—Gly—Phe—SerOH 1.1 mmol (116 mg) of powdered hydrated serine is dissolved in 1 ml of trimethylcyanosilane by heating to between 60° and 80° C. for less than 5 minutes.

To this mixture, a solution of 1 mmol (362 mg) of t-Boc—PheOSucc (phenylalanine protected by a t-Boc group and activated by N-hydroxysuccinimide) in 10 ml of dichloromethane or tetrahydrofuran is added.

After 30 minutes, the active ester has disappeared.

The mixture is poured through a glass sinter charged with 5 g of silica gel, which has been moistened beforehand with 1 ml of water and washed with twice 20 ml of dichloromethane.

Hydrogen chloride is bubbled for 30 seconds through the filtrate, which is then evaporated.

The dipeptide salt collected is redissolved in 2 ml of trimethylcyanosilane at room temperature.

0.98 mmol (275 mg) of Z—GlyOSucc (glycine protected by a Z group and activated by N-hydroxysuccinimide) is then added in 10 ml of dichloromethane.

After 30 minutes at room temperature, the reaction is stopped by adding 10 ml of water, and the precipitate collected is dried.

The yield of Z—Gly—Phe—SerOH is 88% (calculated on Z—GlyOSucc) (350 mg); the product is pure according to all the NMR criteria.

EXAMPLE 3

Preparation of Pro—Phe—Met—AspOH with identification of the intermediate oligopeptides 1st stage: t-Boc—Met—AspOH 150 mg (1.1 mmol) of hydrated aspartic acid is dissolved in 0.5 ml of trimethylcyanosilane at 80° C. in the course of 3 minutes.

346 mg (1.0 mmol) of t-Boc—MetOSucc is added and the mixture is heated to 40° C.

After one hour, a mixture of 250 mg of water in 2 ml of acetonitrile is added. The product is filtered on 5 g of $SiO_2$, as in Example 2 above, and the product obtained is eluted with 30 ml of a solution containing 90% of acetonitrile and 10% of methanol.

The residue is evaporated.

It contains equivalent amounts of N-hydroxysuccinimide and of the desired dipeptide protected by a t-Boc group.

The dipeptide obtained is used as such in the following condensation stage.

2nd stage: t-Boc—Phe—Met—AspOH

Deprotection of the t-Boc dipeptide of stage 1 is carried out by treatment with 0.5 ml of trifluoroacetic acid for one hour at room temperature.

The solution is then evaporated and the residue taken up in 1.0 ml of trimethylcyanosilane.

One equivalent of t-Boc—PheOSucc is added.

The coupling is carried out as described above in the first stage for the dipeptide.

Tripeptide protected by t-Boc is obtained in a yield of more than 95%.

3rd stage: t-Boc—Pro—Phe—Met—AspOH

The procedure described above is repeated using t-Boc—ProOSucc in the condensation stage, and the operations are repeated as described for the first stage.

The N-hydroxysuccinimide formed is trimethylsilylated by adding 0.5 ml of trimethylcyanosilane, and is then evaporated off under vacuum.

The residues are treated with water and then lyophilised.

Pure protected tetrapeptide is obtained in quantitative yield.

EXAMPLE 4

Preparation of t-Boc—Thz—Phe—Met—AspOH

The procedure is as described in Example 3, the first two stages being identical, but in the third stage t-Boc—ThzOSucc is employed in place of t-Boc—ProOSucc.

An almost quantitative yield of tetrapeptide is obtained. The product is pure according to NMR analysis.

A 40:60 mixture of urethane isomers in respect of the t-Boc protecting agent is observed at 0° C.

EXAMPLE 5

Preparation of diZ—Tyr—D—Ala—GlyOH

1st stage: diZ—Tyr—D—AlaOH 449 mg of diZ—TyrOH (hydrated tyrosine protected by a dibenzyloxycarbonyl type group designated diZ) are dissolved in 5 ml of tetrahydrofuran.

0.096 ml of pyradine and 0.173 ml of triethylamine are added, followed by 0.144 ml of trimethylacetic acid chloride (pivaloyl chloride, Piv—Cl) at −10° C. so as to obtain a protected and activated amino acid.

After one minute, 1 g of an ion exchanger, dried in its free carboxyl form (Amberlite IR C 50H), is added in order to trap any excess pivaloyl chloride.

The mixture is stirred for 1 minute at −10° C.

107 mg of D—Ala are dissolved, with heating, in 5 ml of trimethylcyanosilane; the silylated amino acid is obtained and this is added to the above mixture.

The mixture obtained is brought to room temperature and maintained at this temperature for 30 minutes.

The ion exchanger is filtered off and the filtrate is lyophilised.

2 ml of methanol are added and the mixture is evaporated. diZ—Tyr—D—AlaOH is obtained and this is used as it is.

2nd stage: diZ—Tyr—D—Ala—GlyOH

In order to activate it, the protected dipeptide obtained in the first stage is dissolved in 0.096 ml of pyridine and 0.173 ml of triethylamine, followed by addition of 0.144 ml of pivaloyl chloride.

After one minute, 1 g of an ion exchanger, dried in its free carboxyl form, is added and the mixture is stirred for one minute at −10° C.

90 mg of glycine are dissolved in 5 ml of trimethylcyanosilane in order to carry out the silylation. This silylated product obtained is added to the mixture which is maintained for 30 minutes at room temperature.

The ion exchanger is filtered off, the filtrate is lyophilised and 2 ml of methanol are added.

After evaporation, the tripeptide diZ—Tyr—Ala—GlyOH is rapidly crystallised in an ethyl ether/ethyl acetate mixture, giving the tripeptide which is pure by NMR analysis. The yield is 68%.

EXAMPLES 6

Example 6.a: synthesis of [Met$^5$]-enkephalin

[Met$^5$]-enkephalin is a pentapeptide of formula Tyr—Gly—Gly—Phe—Met.

1st stage: synthesis of t-Boc—Gly—Gly—Phe—MetOH 1.75 g (10 mmol) of t-Boc—GlyOH (hydrated glycine protected by a t-Boc group) is dissolved with 1.6 g (20 mmol) of pyridine and 1.0 g (10 mmol) of triethylamine in 20 ml of dried tetrahydrofuran.

The solution is cooled to −10° C., and 1.22 ml (10 mmol) of pivaloyl chloride added to it, so as to carry out the activation stage.

After one minute, there are added 750 mg (10 mmol) of H—GlyOH which are previously dissolved in 6 ml of trimethylcyanosilane and 10 ml of n-hexane, in order to silylate the glycine.

The mixture is evaporated at a temperature above 60° C.

20 ml of toluene and 1 ml of trimethylcyanosilane are added, and the mixture is again evaporated under vacuum in order to remove the excess pivaloyl chloride.

The residue is dissolved in 20 ml of methanol and then evaporated.

The residue is dissolved in 20 ml of toluene and then evaporated.

The dipeptide t-Boc—Gly—GlyOH obtained is directly acted with pivaloyl chloride and then coupled with silylated PheOH as described above.

The tripeptide t-Boc—Gly—Gly—PheOH obtained is activated and then coupled with silylated MetOh under the same conditions as described above.

The final residue is dissolved in 100 ml of ethyl acetate and 10 ml of ethanol, and is then washed with 50 ml of 50% strength citric acid in water.

The ethyl acetate phase is dried over magnensium sulphate and then evaporated. The residue is recrystallised in an ethyl acetate/ethyl ether mixture.

The tetrapeptide t-Boc—Gly—Gly—Phe—MetOH is obtained pure according to the criteria of NMR.

The yield is 63% (3.25 g).

2nd stage: synthesis of [Met$^5$]-enkephalin 510 mg (1 mmol) of the tetrapeptide protected by a t-Boc group, obtained in the first stage, are dissolved in 2 ml of trifluoroacetic acid (Tfa) which contains 15% of ethanethiol by volume.

The solution is kept for 2 hours at room temperature and then heated for 15 minutes to 40° C.

After evaporation, quantitative formation of Tfa—H$_3$N$^\oplus$—Gly—Gly—Phe—MetOH is obtained.

To this product there are added 415 mg (1.1 mmol) of t-Boc—OH—Tyr—OSucc with 2 ml of trimethylcyanosilane and 2 ml of tetrahydrofuran.

The tetrapeptide salt is gradually solubilised, and is then subjected for 30 minutes to ultrasound with stirring under vacuum at 0° C., and a clear solution is thereby obtained. After two hours at room temperature, the reaction is complete and the mixture has solidified.

The solid is dissolved in 5 ml of tetrahydrofuran.

The excess t-Boc—(OTMS)Tyr—OSucc is removed by adding 1 g of aminopropyl-silica gel (5.40μ, 3 meq NH$_2$/g).

After 30 minutes, the product is filtered.

The filtrate is treated with 20 ml of methanol.

The product is evaporated.

The yield obtained in this second stage is 95%.

The pentapeptide protected by t-Boc is recrystallised in an ethyl acetate/ethyl ether mixture.

The pentapeptide is obtained pure according to the criteria of NMR. The total yield is 60%.

The pentapeptide [Met$^5$]-enkephalin is deprotected by treatment with trifluoroacetic acid followed by evaporation under vacuum, the corresponding salt being obtained.

EXAMPLE 6.b synthesis of [Leu$^5$]-enkephalin

[Leu$^5$]-enkephalin is a pentapeptide of formula Tyr—Gly—Gly—Phe—Leu.

The synthesis is performed in the same manner as described in Example 6.a above, but with methionine replaced by Leucine.

EXAMPLES 7 AND 7R

Synthesis of t-Boc—Gly—Gly—Phe—MetOH

Example 7 is performed according to the invention, Example 7R is a comparative example for Example 7 which uses trimethylchlorosilane in place of trimethylcyanosilane.

EXAMPLE 7

Synthesis of t-Boc—Gly—Gly—Phe—MetOH 5 mmol of t-Boc—GlyOH (hydrated glycine protected by a t-Boc group) dissolved in 5 mmol of triethylamine, 5 mmol of pyridine and 20 ml of tetrahydrofuran are placed in a 500-ml flask.

The solution is cooled to −15° C. and 5 mmol of pivaloyl chloride are added to it with stirring, so as to carry out the activation stage.

After 2 minutes, 5.5 mmol of persilylated glycine, obtained by dissolving H—GlyOH in 3 ml of trimethlcyanosilane and 5 ml of n-hexane, are added.

The solution is brought back to room temperature, and then evaporated under reduced pressure in order to separate off the volatile silylated components.

The solution is treated with 30 ml of toluene and then evaporated to dryness; this is repeated once with a further 30 ml of toluene.

The residue is dissolved in a methanol/toluene (1:1) mixture and then evaporated.

The residue is again treated twice with 30 ml of toluene and then evaporated to dryness in order to remove all trace of excess methanol.

The dipeptide t-Boc—Gly—GlyOH obtained is directly activated with pivaloyl chloride and then coupled with silylated PheOH, as described above.

The tripeptide t-Boc—Gly—Gly—PheOH obtained is activated and then coupled with silylated MetOH under the same conditions as described above.

The final residue on evaporation contains t-Boc—Gly—Gly—Phe—MetOH.

The latter is dissolved in 100 ml of ethyl acetate in 20 ml of methanol, and then washed successively with water and phosphoric acid (pH approximately 2).

The residue on evaporation is recrystallised, first in dichloromethane, and secondly in an ethyl acetate-/ethyl ether mixture.

The tetrapeptide is obtained pure according to the criteria of NMR.

The yield is 63%.

EXAMPLE 7R

Comparative Example

Synthesis of t-Boc—Gly—Gly—Phe—MetOH using trimethylchlorosilane as silylating agent 1st stage: silylation of each amino acid
(a) Methionine
To 5 mmol of methionine in zwitterionic form, 10 mmol of triethylamine are added in 2 ml of trimethylchlorosilane. To this mixture, 25 ml of dried trichloromethane are added. This mixture is heated until clear solutions are obtained.

The triethylamine hydrochloride formed is removed by filtration under nitrogen after precipitation with dried toluene.

After filtration, the solution is reduced to a volume of approximately 20 ml and used as it is.

the silylation of methionine is accomplished in 3 hours at room temperature by this method.

(b) Glycine

Silylation of glycine is carried out in the same manner as that of glycine described in Example (a) above; but this amino acid requires a refluxing stage.

(c) Phenylalanine

The silylation of phenylalanine is carried out in the same manner as that of methionine described in Example (a) above, but this amino acid requires a refluxing stage.

2nd stage: activation 5 mmol of t-Boc—GlyOH dissolved in 5 mmol of triethylamine, 5 mmol of pyridine and 20 ml of tetrahydrofuran are placed in a 500-ml flask.

The solution is cooled to $-15°$ C. and 5 mmol of pivaloyl chloride are added to it with stirring.

After 2 minutes, a solution of 5.5 mmol of persilylated glycine, obtained in the first stage, are added.

The solution is brought back to room temperature, and then evaporated under reduced pressure for the purpose of separating-off the volatile silylated components.

The solution is treated with 30 ml of toluene and then evaporated to dryness; this is repeated once with a further 30 ml of toluene.

The residue is dissolved in a methanol/toluene (1:1) mixture; it is then evaporated.

The residue is again treated twice with 30 ml of toluene, and then evaporated to dryness in order to remove all trace of excess methanol.

The residue on evaporation is used as it is in the subsequent coupling stage.

The same procedure is followed with the solution of persilylated phenylalanine in place of glycine, and then with the solution of persilylated methionine, the activation stage in this case requiring 10 minutes at $-15°$ C.

3rd stage: coupling

The final residue on evaporation contains t-Boc—Gly—Gly—Phe—MetOH.

The latter is dissolved in 100 ml of ethyl acetate and 20 ml of methanol, and then washed successively with water and phosphoric acid (pH approximately 2).

The residue on evaporation is recrystallised, first in dichloromethane, and secondly in an ethyl acetate/ethyl ether mixture.

The tetrapeptide is obtained pure according to the criteria of NMR.

The yield is 28%.

A comparison of Example 7 and Example 7R shows the distinct difference in yield obtained; furthermore, carrying out Example 7R requires a succession of more complex operations (heating, filtration, evaporation) than Example 7; most especially, in Example 7R, the formation of triethylamine hydrochloride (salts) is a nuisance; this product has to be removed by filtration after addition of toluene, and these operations require working conditions in a very dry atmosphere.

What is claimed is:

1. In a process for synthesising peptides from amino acids which have been silylated with the participation of trialkylsilane silylating agents, the improvement comprising using trialkylcyanosilanes of general formula (A)

in which $R_1$, $R_2$ and $R_3$ denote, independently of each other, alkyl groups which can be identical or different and which contain from 1 to 3 carbon atoms.

2. Process according to claim 1, wherein the trialkylcyanosilanes are used to form peptide bonds between the amino acids.

3. Process according to claim 1, wherein the three alkyl groups $R_1$, $R_2$ and $R_3$ contain 1 or 2 carbon atoms.

4. Process according to claim 3, wherein the three alkyl groups $R_1$, $R_2$ and $R_3$ are identical.

5. Process according to claim 4, wherein the trialkylcyanosilane used is trimethylcyanosilane.

6. Process according to claim 1, wherein from 20 ml to 0.01 ml of trialkylcyanosilane are employed per mmol of amino acid.

7. Process according to claim 5, wherein from 5 to 0.1 ml of trimethylcyanosilane are employed per mmol of amino acid.

* * * * *